(12) United States Patent
Zhang et al.

(10) Patent No.: US 9,504,850 B2
(45) Date of Patent: Nov. 29, 2016

(54) METHODS AND SYSTEM FOR BREATHING-SYNCHRONIZED, TARGET-TRACKING RADIATION THERAPY

(71) Applicant: XCISION MEDICAL SYSTEMS, LLC, Columbia, MD (US)

(72) Inventors: Jin Zhang, Catonsville, MD (US); Xinsheng Cedric Yu, Pasadena, MD (US); Peter Maton, Columbia, MD (US)

(73) Assignee: XCISION MEDICAL SYSTEMS LLC, Columbia, MD (US)

( * ) Notice: Subject to any disclaimer, the term of this patent is extended or adjusted under 35 U.S.C. 154(b) by 118 days.

(21) Appl. No.: 14/201,906

(22) Filed: Mar. 9, 2014

(65) Prior Publication Data

US 2014/0275704 A1    Sep. 18, 2014

Related U.S. Application Data

(60) Provisional application No. 61/786,006, filed on Mar. 14, 2013.

(51) Int. Cl.
*A61N 5/10* (2006.01)
*A61B 5/113* (2006.01)
*A61B 5/00* (2006.01)
(Continued)

(52) U.S. Cl.
CPC ............ *A61N 5/1037* (2013.01); *A61B 5/4836* (2013.01); *A61N 5/1049* (2013.01); *A61N 5/1067* (2013.01); *A61B 5/087* (2013.01);
(Continued)

(58) Field of Classification Search
CPC .............. A61N 5/1037; A61N 5/1045; A61N 5/1049; A61N 5/1067; A61N 5/1068; A61B 6/032; A61B 5/4836; A61B 5/087; A61B 5/1135
See application file for complete search history.

(56) References Cited

U.S. PATENT DOCUMENTS 7,822,176 B2   10/2010  Yi et al.
2008/0144772 A1*  6/2008  Yi .................... A61N 5/1049
                                                        378/65

OTHER PUBLICATIONS

Coolens et al., "A margin model to account for respiration-induced tumour motion and its variability," *Phys. Med. Biol.*, 53: 4317-4330 (2008).

(Continued)

*Primary Examiner* — Christine H Matthews
*Assistant Examiner* — Joshua D Lannu
(74) *Attorney, Agent, or Firm* — Carol Larcher; Larcher & Chao Law Group

(57) ABSTRACT

Preparing a plan to synchronize radiation delivery to a target in a patient with patient breathing phase and amplitude as the independent variable comprising (a) obtaining simultaneous data on patient breathing and target shape and location, (b) correlating the data and optimizing the correlation, (c) establishing optimal parameters of radiation delivery for each breathing phase/amplitude or for each target shape/location; and (d) synchronizing radiation delivery to a target in a patient with patient breathing comprising (a) positioning the patient, (b) monitoring actual breathing or the shape/location of the target, and (c) while monitoring, delivering radiation to the target according to a plan; and a system for controlling radiation delivery by a device to a target in a patient comprising (i) a processor, which receives and processes data on breathing or the shape/location of the target, and (ii) a controller, which controls radiation delivery to the target according to a plan, which synchronizes radiation delivery to the target with breathing data or the shape/location of the target.

16 Claims, 6 Drawing Sheets

(51) Int. Cl.
*A61B 6/03* (2006.01)
*A61B 5/087* (2006.01)

(52) U.S. Cl.
CPC .............. *A61B5/1135* (2013.01); *A61B 6/032* (2013.01); *A61N 5/1045* (2013.01); *A61N 5/1068* (2013.01)

(56) References Cited

OTHER PUBLICATIONS

D'Souza et al., "Real-time intra-fraction-motion tracking using the treatment couch: a feasibility study," *Phys. Med. Biol.*, 50: 4021-4033 (2005).

Ford et al., "Respiration-correlated spiral CT: A method of measuring respiratory induced anatomic motion for radiation treatment planning," *Med. Phys.*, 30: 88-97 (2003).

Keall et al., "Motion Adaptive X-Ray Therapy: A Feasibility Study," *Phys. Med. Biol.*, 46:1-10 (2001).

Korreman et al., "Breathing Adapted Radiotherapy for Breast Cancer: Comparison of Free Breathing Gating with the Breath-hold Technique," *Radiother. Oncol.*, 76: 311-318 (2005).

Kubo et al., "Respiration gated radiotherapy treatment: a technical study," *Phys. Med. Biol.*, 41: 83-91 (1996).

Shirato et al., "Physical Aspects of a Real-time Tumor-tracking System for Gated Radiotherapy," *Int. J. Radiat. Oncol., Biol., Phys.*, 48: 1187-1195 (2004).

Wong et al., "The Use of Active Breathing Control (ABC) to Reduce Margin for Breathing Motion," *Int. J. Radiat. Oncol. Biol. Phys.*, 44: 911-919 (1999).

Yi et al., "Real-time tumor tracking with preprogrammed dynamic multileaf-collimator motion and adaptive dose-rate regulation," *Med. Phys.*, 35: 3955-3962 (2008).

\* cited by examiner

METHODS AND SYSTEM FOR BREATHING-SYNCHRONIZED, TARGET-TRACKING RADIATION THERAPY

TECHNICAL FIELD

The present disclosure relates to radiation therapy, in particular methods and a system for planning and delivering radiation therapy. The methods and system involve synchronizing tracking of a target, e.g., a tumor, in a patient with the patient's breathing.

BACKGROUND

Radiation therapy is used to treat cancers and other conditions in patients. One commonly used form of radiation therapy is external beam radiation therapy. In external beam radiation therapy, a high-energy, x-ray beam generated by a machine, usually a linear accelerator (linac), which is located outside of the patient's body, is directed at a tumor or cancerous cells (i.e., the "target") inside the patient's body. While the radiation kills the cancerous cells, it also harms normal tissue and organs in the vicinity of the tumor/cancerous cells in the patient. Thus, the goal in radiation therapy is to deliver the required dose of radiation to the target volume, while minimizing the radiation dose to surrounding normal tissue that may cause complications and harm to the patient.

When delivering radiation treatment to a target, geometric accuracy of the delivery of radiation is the key to irradiating the target and minimizing the collateral damage to surrounding normal tissues and structures. It is difficult, however, to achieve the necessary geometric accuracy when the target is moving as the patient is breathing.

The simplest method for dealing with breathing-induced target motion is to have the radiation beam wide enough to cover all possible regions to which the target can move. In the art of radiation therapy, this is referred to as the "addition of treatment margin". The expanded target is called the "internal target volume" (ITV). This approach, however, results in the inclusion of a significant amount of normal tissues to the treatment volume, leading to an increase in collateral damage and greater toxicity (Coolens et al., Phys. Med. Biol. 53: 4317-4330 (2008)).

Another method that has been attempted to reduce the error due to target motion is to have the patient hold his breath when the target is being irradiated (Korreman et al., Radiother. Oncol. 76: 311-318 (2005)). Since the target is only irradiated when the patient is holding his breath, more time is required to administer treatment because the delivery of radiation is limited to when the patient is holding his breath and the length of time for which the breath can be held. Furthermore, if the desired time at which the breath should be held for optimal irradiation of the target is at the end of exhale, the patient may not be able to hold his breath accurately. In addition, it can be very difficult, if not impossible, to expect a patient with compromised lung function, such as a patient with lung cancer, to hold his breath at all, let alone for a length of time sufficient to deliver radiation to a target.

Another commonly used method that has been utilized to reduce error due to target motion is "gating". In this method, the radiation beam aperture is reduced to focus on a discrete, pre-selected region of the target at a particular time window during the patient's breathing cycle (Kubo et al., Phys. Med. Biol. 41: 83-91 (1996)). It is assumed that the target motion correlates with the breathing cycle, such that the tumor will return to the treatment position at the same time window of the breathing cycle, during the entire course of therapy. A sensor monitors a patient's breath or abdominal excursion (during breathing) and triggers the delivery of a pulse of radiation at the pre-selected time window. The time window may be selected when the patient's lungs are nearly full as the patient inhales (or, alternatively, when the patient's lungs are nearly empty as the patient exhales). Since radiation is delivered during only a portion (typically 30-40%) of a patient's breathing cycle, the technique is time-consuming and, therefore, not optimal. The duty cycles of such systems are low. In addition, the tumor also moves within the time window, although less than its full range of motion. Therefore, a residual margin is still required to ensure that the tumor gets the intended dose of radiation.

Yet another method that has been explored for reducing error due to respiratory motion is "tumor tracking". In target tracking, the radiation beam follows the respiratory motion of the tumor. At least four different tracking techniques are currently being implemented or studied.

The first tracking technique involves moving the entire treatment head to track the tumor motion. In existing commercial radiotherapy devices a robotic arm is used to carry the linac around the patient to track the target during the radiation beam delivery. This technique can dynamically adjust to changes in patient breathing patterns. However, it is impossible for non-robotic, commercially available linear accelerator systems to emulate such a method. Notably, only a small fraction of all linear accelerators or external beam radiation equipment has such robotic capability, and therefore, its widespread use is expected to be limited.

The second tracking technique employs static radiotherapy units, which track the tumor with guided breathing (Wong et al., Int. J. Radiat. Oncol. Biol. Phys. 44: 911-919 (1999)). Implementation requires a patient to follow a fixed breathing pattern to match motion of a radiation beam that is pre-programmed according to the guided breathing pattern. This scheme has problems in that most patients are incapable of breathing without irregularities, even after extensive training and with the assistance of audio or video breathing guidance.

A third variant of tumor tracking, which uses a static linac, tracks target motion in real-time and compensates by immediately moving the multi-leaf collimator (MLC) (Keall et al., Phys. Med. Biol. 46: 1-10 (2001)) or the treatment table (D'Souza et al., Phys. Med. Biol. 50: 4021-33 (2005)) to a new, unplanned position in accordance with the detected respiratory target motion. Such an approach requires a quick-responding MLC or table mechanism that would be only possible by the addition of specialized equipment, which is unavailable commercially. Furthermore, such techniques require real-time treatment dose computation and treatment quality verification. Even if tumor position is readily ascertainable, re-definition of live tumor shape changes is necessary and expected to be very difficult, thereby further complicating MLC shape re-configuration. As a result, controlling the movement of the beam to track the tumor is difficult to implement in real-time. Furthermore, this technique also presents a safety issue as the chance for error in calculations performed in real-time increases.

The fourth and more practical method of tumor tracking is described by Yi et al. in U.S. Pat. No. 7,822,716 B2, namely "dose-rate regulated tracking" (DRRT) (see, also, Yi et al., Med. Phys. 35: 3955-3962 (2008)). In DRRT a radiation beam is delivered to a moving target using a pre-programmed MLC sequence designed to track an expected, regular tumor motion trajectory based on tumor motion and breathing pattern data obtained from a four-dimensional (4-D) computed tomography (CT) scan of a patient in need of radiation therapy. Irregularities in the frequency of patient breathing are detected in real-time during treatment delivery, and the information is used to adjust the linac's dose rate to speed-up or slow-down radiation delivery. Although it handles variations in breathing frequency very well, DRRT does not handle variations in breathing amplitude very well, especially for amplitudes not planned based on regular breathing, such as when the patient occasionally inhales or exhales deeply.

Except for methods that resort to brute force, all previous methods for handling breathing-induced tumor motions are bounded by how the linear accelerator treatment delivery is controlled. The treatment delivery is conventionally controlled by a set of treatment parameters including dynamic beam delivery components such as, but not limited to, each leaf position of the MLC, the MLC carriage, the field size (or collimator opening), the gantry angle, the table position, and the collimator angle, etc. All planned motions of the MLC, the collimator jaws, and the gantry and other parameters are enslaved to the delivered monitor units (MUs), i.e., the treatment delivery machine's internal unit for tracking the amount of radiation sent through its monitoring ion chamber. The relationship between MU and dose in the medium is calibrated by the user.

Thus, the above methods suffer from various disadvantages, such as a need for large robotic linac translation hardware, challenges in determining new beam locations, an MLC design that can adjust rapidly to a new target position in real-time, new hardware to shift a treatment table during beam delivery, and/or a need for a patient to follow a strict breathing sequence, which cannot be achieved even with training and guidance. While these issues are addressed to a significant extent by the DRRT method of Yi et al. by ensuring that the radiation beam of a radiotherapy device is continuously (or nearly continuously) directed at the target, DRRT requires the treatment to follow a preprogrammed treatment sequence that is a function of the delivered MUs. The preprogrammed beam motion sequence is derived by assuming that the patient breathes in a regular pattern while being irradiated, and deviations in the patient's breathing period (i.e., speed) are handled by speeding up or slowing down delivery with dose rate control. Therefore, DRRT requires the linac to vary dose rate in real-time—a capability not readily available for all linear accelerator designs. Moreover, because dose rate control can only vary the speed of the delivery, DRRT does not enable handling deviations in the patient's breathing amplitude. While it is theoretically easier to adjust dose rate when the electron gun is "gated", it is difficult to make quick and accurate adjustments when more efficient "non-gated" electron guns are used as the source of electrons being accelerated.

In view of the foregoing, it is an object of the present disclosure to provide methods and a system for target tracking that do not suffer from the disadvantages attendant the methods of the prior art. This and other objects and advantages, as well as inventive features, will become apparent from the detailed description provided herein.

SUMMARY

A method of preparing a plan to synchronize delivery of radiation to a target in a patient with expected breathing of the patient is provided. The method comprises: (a) obtaining simultaneous data on the breathing of the patient and the tracking of a target in the patient, wherein the data on the breathing of the patient includes frequency of breaths and amplitude of breaths and the data on the tracking of a target includes location of the target and shape of the target, (b) correlating the data on the breathing of the patient and the tracking of a target in the patient and optimizing the correlation, and (c) establishing optimal parameters for the delivery of radiation to the target in the patient in view of the optimized correlation of (b).

Preferably, the data were previously generated using free-breathing imaging. The free-breathing imaging can be conducted using a four-dimensional (4-D) computed tomography (CT) scan.

With regard to the above method of preparing a plan, the optimal parameters for the delivery of radiation to the target can be established based on a reference image set generated for an initial breathing phase using free-breathing imaging. The optimal parameters for the delivery of radiation to the target for a sequential breathing phase can be established using the optimal parameters for the initial breathing phase as initial input into an inverse planning algorithm, and the optimal parameters for each subsequent sequential breathing phase can be established using the optimal parameters for the previous sequential breathing phase, while enforcing a field connectivity constraint between the optimal parameters for immediately sequential breathing phases. The field connectivity constraint can be the shape of the field of radiation.

Alternatively, with regard to the above method of preparing a plan, the optimal parameters for the delivery of radiation to the target can be established based on a reference image set generated for each phase of a breathing cycle using free-breathing imaging. A radiation dose efficiency index can be assigned to each phase of a breathing cycle, or the optimal parameters for the delivery of radiation to the target for each sequential breathing phase are established while enforcing a field connectivity constraint between immediately sequential breathing phases by applying an algorithm of directly transforming a parameter between immediately sequential breathing phases.

Further provided is a method of synchronizing delivery of radiation to a target in a patient that moves with breathing of the patient. The method comprises: (a) positioning the patient for delivery of radiation to a target in the patient, (b) either monitoring the actual breathing of the patient in real time via an external indicator of internal target motion or monitoring directly in real time the shape and/or location of the target within the patient, and (c) while continuing to monitor the actual breathing of the patient or the shape and/or location of the target, delivering radiation to the target in the patient according to a radiation treatment plan that defines the radiation delivery parameters as a function of the breathing phase and amplitude, thereby achieving tracking of the target. The radiation treatment plan was prepared by a method comprising: (i) obtaining simultaneous data on the frequency and amplitude of the breathing of the patient and the shape and location of a target in the patient, (ii) correlating the data on the breathing of the patient and the shape and/or location of a target in the patient and optimizing the correlation, and (iii) establishing optimal parameters for the radiation to be delivered to the target in the patient in view of the optimized correlation of (ii). Unlike other treatment schemes proposed for tumor tracking, the treatment scheme developed according to the disclosure does not define a delivery sequence as a function of time or machine monitor units (MU) but, rather, specifies the treatment delivery parameters, such as beam aperture shape and location, that are to exist as a function of the phase/amplitude of breathing at any point in time during an episode of treatment delivery.

This specification is achieved during treatment planning, whereby an array of one-to-one relationships between the phase/amplitude of breathing and the shape/location of the target is established. Specifically, the variation in shape/location of the target with the phase/amplitude of breathing is used to determine the required variation in treatment parameters with phase/amplitude of breathing. Subsequently, during treatment delivery, treatment parameters are varied according to the unique breathing pattern of the patient during that period of time. A key distinction to all dynamic treatment plans of the prior art is that the beam's aperture shape and location are not enslaved in a synchronous manner to the delivered radiation monitor units (MUs), but rather are synchronized in real time with the breathing phase and/or amplitude that uniquely exists during an episode of treatment delivery. Hence, we refer to the method of this disclosure as breathing-synchronized tumor tracking.

Preferably, the data of (i) were previously generated using free-breathing imaging. The free-breathing imaging can be conducted using a four-dimensional (4-D) computed tomography (CT) scan.

With regard to the above method of synchronizing delivery, the optimal parameters for the delivery of radiation to the target can be established based on a reference image set generated for an initial breathing phase using free-breathing imaging. The optimal parameters for the delivery of radiation to the target for a sequential breathing phase can be established using the optimal parameters for the initial breathing phase as initial input into an inverse planning algorithm, and the optimal parameters for each subsequent sequential breathing phase can be established using the optimal parameters for the previous sequential breathing phase, while enforcing a field connectivity constraint between the optimal parameters for immediately sequential breathing phases. The field connectivity constraint can be the shape of the field of radiation.

Alternatively, with regard to the above method of synchronizing delivery, the optimal parameters for the delivery of radiation to the target can be established based on a reference image set generated for each phase of a breathing cycle using free-breathing imaging. A radiation dose efficiency index can be assigned to each phase of a breathing cycle, or the optimal parameters for the delivery of radiation to the target for each sequential breathing phase are established while enforcing a field connectivity constraint between immediately sequential breathing phases by applying an algorithm of directly transforming a parameter between immediately sequential breathing phases.

Still further provided is a system for controlling delivery of radiation by a radiation delivery device to a moving target in a patient in accordance with a radiation treatment plan. The system comprises: (i) a processor, which receives and processes data on the actual breathing of the patient or the shape and/or location of the target, wherein the data on the actual breathing of the patient includes breathing frequency and breathing amplitude, and (ii) a controller, which controls delivery of radiation by the radiation delivery device to the moving target in the patient in accordance with a radiation treatment plan, which defines the shape and location of the beam aperture for each breathing amplitude and location or for each shape and location of the target, thereby the synchronization of the movement of the radiation beam and the movement of the target in the patient is ensured. In the field of radiation therapy, such synchronization is said to have achieved tumor tracking.

Preferably, and even desirably, the controller adjusts at least one optimal parameter for the delivery of radiation by the radiation delivery device to the moving target for each phase of the breathing within a breathing cycle of the patient, wherein the optimal parameter is not enslaved to monitor units (MU) but, rather, synchronized in real time with breathing. Preferably, and even desirably, the radiation treatment plan was prepared by a method comprising: (i) obtaining simultaneous data on the breathing of the patient and the shape and location of the target in the patient, wherein the data on the breathing of the patient includes frequency of breaths and amplitude of breaths, (ii) correlating the data on the breathing of the patient and the shape and/or location of a target in the patient and optimizing the correlation, and (iii) establishing optimal parameters for the radiation to be delivered to the target in the patient in view of the optimized correlation of (ii).

The data of (i) can be previously generated using free-breathing imaging. The free-breathing imaging can be conducted using a four-dimensional (4-D) computed tomography (CT) scan.

The optimal parameters for the delivery of radiation to the target can be established based on a reference image set generated for an initial breathing phase using free-breathing imaging. The optimal parameters for the delivery of radiation to the target for a sequential breathing phase can be established using the optimal parameters for the initial breathing phase as initial input into an inverse planning algorithm, and the optimal parameters for each subsequent sequential breathing phase can be established using the optimal parameters for the previous sequential breathing phase, while enforcing a field connectivity constraint between the optimal parameters for immediately sequential breathing phases. The field connectivity constraint is defined by the physical ability of the radiation delivery device, such as how fast the aperture shape can change. Enforcing such constraint in the planning process ensures that the aperture shapes and locations from one breathing phase to the next can be smoothly transitioned.

The optimal parameters for the delivery of radiation to the target can be established based on a reference image set generated for each phase interval of a breathing cycle using free-breathing imaging. For each phase of the breathing cycle, a plan is generated based on the corresponding image set. For each such plan, optimized beam parameters are generated as though the treatment will be delivered entirely at that phase. During treatment delivery, the beam parameters corresponding to each phase will be utilized for the duration of a phase interval detected in real time. Based on a reference plan for an initial phase, a known dose integrated throughout the target is to be delivered for a given beam. For each phase-specific plan the rate of accumulation of such an integrated dose for a given beam is known as a function of MU delivered. It is, therefore, possible to keep track of the integrated dose for a given beam during treatment delivery as the phase-specific beams are cycled through. Treatment delivery for the given beam can, therefore, be terminated when the required integrated dose has been delivered. This principle equally applies to a beam comprised of multiple segments, whereby the required integrated dose for each segment is known and the corresponding phase-specific segments are cycled through until the required integrated dose has been delivered.

DETAILED DESCRIPTION

Figure 1:
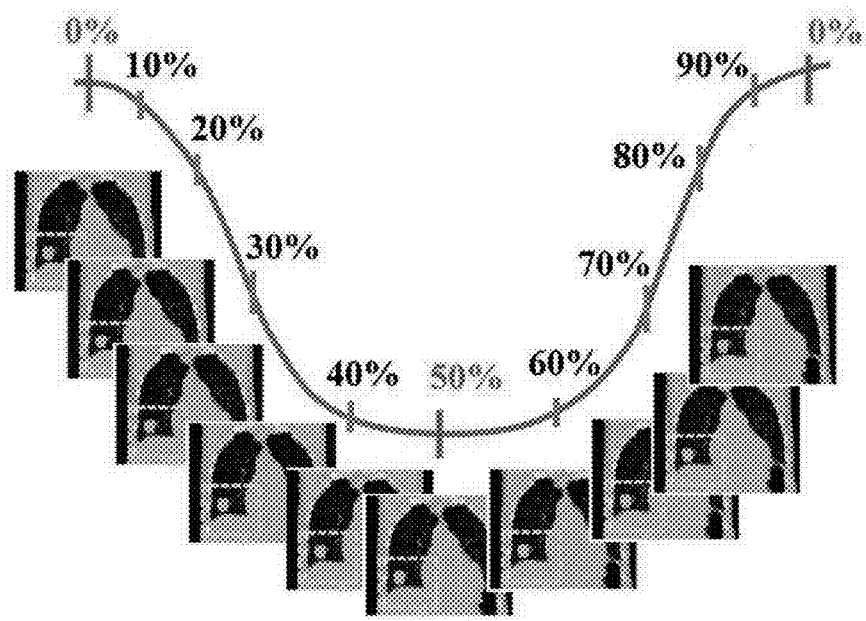
FIG. 1 is an exemplary data set (10 data sets) for a four-dimensional (4-D) computed tomography (CT) scan, wherein each CT slide was time-stamped in accordance with the patient's breathing signal and represents one phase of the respiration cycle.

The present disclosure is predicated, at least in part, on the most natural way to handle breathing-induced tumor motion during radiation therapy. The location and shape of a tumor have been shown to correlate well with a patient's breathing pattern (Ford et al., Med. Phys. 30: 88-97 (2003); and Shirato et al., Int. J. Radiat. Oncol., Biol., Phys. 48: 1187-1195 (2004)). In view of the foregoing, a method and a system are provided. Delivery of radiation therapy is controlled directly by the patient's breathing, by way of a breathing signal/surrogate. The breathing-generated signal is directly used as the treatment machine's internal parameter to guide a radiation beam to track target (e.g., tumor) motion. The method is referred to herein as "breathing-synchronized, target-tracking " or BSTT.

The following definitions are relevant to the present disclosure:

(a) "Breathing cycle" or "respiratory cycle" refers to the time between a given phase of one breathing cycle and the given phase in the consecutive breathing cycle. For example, a breathing cycle can refer, and typically does refer, to the time between an inspiration of one breathing cycle and the inspiration of the consecutive breathing cycle.

(b) "Inhalation" or "inspiration" is a phase of the breathing cycle characterized by the flow of air into the lungs ("positive air flow"). While air flows into the lungs, the respiratory volume increases. Inhalation ends when positive air flow is zero.

(c) "Exhalation" or "expiration" is a phase of the breathing cycle characterized by the flow of air out of the lungs ("negative air flow"). While air flows out of the lungs, the respiratory volume decreases. Exhalation ends when negative air flow is zero.

(d) "Period of rest" or "pause" is a phase of the breathing cycle between the end of an exhalation and the beginning of an inhalation.

The terminology used herein is for the purpose of describing particular embodiments only and is not otherwise intended to be limiting.

A method of preparing a plan to synchronize delivery of radiation to a target in a patient with expected breathing of the patient is provided. The method comprises: (a) obtaining simultaneous data on the breathing of the patient and the tracking of a target in the patient, wherein the data on the breathing of the patient includes frequency of breaths and amplitude of breaths and the data on the tracking of a target includes location of the target and shape of the target, (b) correlating the data on the breathing of the patient and the tracking of a target in the patient and optimizing the correlation, and (c) establishing optimal parameters for the delivery of radiation to the target in the patient in view of the optimized correlation of (b).

Preferably, the data were previously generated using free-breathing imaging. The free-breathing imaging can be conducted using a four-dimensional (4-D) computed tomography (CT) scan.

The optimal parameters for the delivery of radiation to the target can be established based on a reference image set generated for an initial breathing phase using free-breathing imaging. The optimal parameters for the delivery of radiation to the target for a sequential breathing phase can be established using the optimal parameters for the initial breathing phase as initial input into an inverse planning algorithm, and the optimal parameters for each subsequent sequential breathing phase can be established using the optimal parameters for the previous sequential breathing phase, while enforcing a field connectivity constraint between the optimal parameters for immediately sequential breathing phases. The field connectivity constraint can be the shape of the field of radiation.

Alternatively, the optimal parameters for the delivery of radiation to the target can be established based on a reference image set generated for each phase of a breathing cycle using free-breathing imaging. A radiation dose efficiency index can be assigned to each phase of a breathing cycle, or the optimal parameters for the delivery of radiation to the target for each sequential breathing phase are established while enforcing a field connectivity constraint between immediately sequential breathing phases by applying an algorithm of directly transforming a parameter between immediately sequential breathing phases.

Further provided is a method of synchronizing delivery of radiation to a target in a patient with breathing of the patient. The method comprises: (a) positioning the patient for delivery of radiation to a target in the patient, (b) either monitoring the actual breathing of the patient in real time via an external indicator of internal target motion or monitoring directly in real time the shape and/or location of the target within the patient, and (c) while continuing to monitor the actual breathing of the patient or the shape and/or location of the target, delivering radiation to the target in the patient according to a radiation treatment plan in view of the actual breathing of the patient or the tracking of the target, wherein the radiation treatment plan was prepared by a method comprising: (i) obtaining simultaneous data on the breathing of the patient and the tracking of a target in the patient, wherein the data on the breathing of the patient includes frequency of breaths and amplitude of breaths and the data on the tracking of a target includes location of the target and shape of the target, (ii) correlating the data on the breathing of the patient and the tracking of a target in the patient and optimizing the correlation, and (iii) establishing optimal parameters for the radiation to be delivered to the target in the patient in view of the optimized correlation of (ii).

Preferably, the data of (i) were previously generated using free-breathing imaging. The free-breathing imaging can be conducted using a four-dimensional (4-D) computed tomography (CT) scan.

The optimal parameters for the delivery of radiation to the target can be established based on a reference image set generated for an initial breathing phase using free-breathing imaging. The optimal parameters for the delivery of radiation to the target for a sequential breathing phase can be established using the optimal parameters for the initial breathing phase as initial input into an inverse planning algorithm, and the optimal parameters for each subsequent sequential breathing phase can be established using the optimal parameters for the previous sequential breathing phase, while enforcing a field connectivity constraint between the optimal parameters for immediately sequential breathing phases. The field connectivity constraint can be the shape of the field of radiation.

Alternatively, the optimal parameters for the delivery of radiation to the target can be established based on a reference image set generated for each phase of a breathing cycle using free-breathing imaging. A radiation dose efficiency index can be assigned to each phase of a breathing cycle, or the optimal parameters for the delivery of radiation to the target for each sequential breathing phase are established while enforcing a field connectivity constraint between immediately sequential breathing phases by applying an algorithm of directly transforming a parameter between immediately sequential breathing phases.

The method relies on simultaneous data on the patient's breathing (i.e., frequency and amplitude) and the patient's anatomy (i.e., target location and shape during breathing) previously generated through a free-breathing imaging study, such as by using a four-dimensional (4-D) computed tomography (CT) scan. Preferably, and even desirably, the data are obtained as close in time as reasonably possible to the time of radiation therapy. Preferably, the data are fed into the BSTT system in real time. In this regard, the manner in which the data on patient breathing are obtained is not critical to the method and the system. Any suitable method of obtaining data on patient breathing can be used. Examples of such methods include, but are not limited to, direct methods, such as on-board imaging of the target, itself, or indirect methods, such as a strain gauge that measures chest wall expansion, a spirometer that measures tidal lung volume, or other means to track chest wall or abdominal movement. For ease of reference, "real-time breathing sensor" will be used herein to refer to a device that generates data on patient breathing, including, but not limited to, breath amplitude and breath frequency (amplitude over time). Although the breathing signal is periodic, the amplitude and the frequency of the breathing signal can vary over the course of a real-time measurement, such as that which is exemplified in FIG. 2, which is a graph of gating amplitude (cm) versus time (sec). Preferably, and even desirably, the manner in which real-time breathing is monitored during radiation therapy is the same as the manner in which patient breathing was monitored prior to radiation therapy. Irrespective of the method used to obtain data on patient breathing, the method comprises correlating breathing phase/amplitude and target shape/location through an optimization process, which, in turn, allows the relationship between the radiation beam aperture shape/location and the breathing phase/amplitude to be optimized before treatment delivery. All treatment parameters in BSTT are directly controlled by the real-time patient breathing signal, instead of being enslaved to the delivered MUs. In this regard, the method and system of the present disclosure overcome disadvantages inherent in the methods of the prior art, including the inability of DRRT to handle variations in both of breathing amplitude and breathing frequency and the time-consuming computation of radiation beam aperture shape and location "on-the-fly", which consequently can render field shapes/locations less than optimal for the best composite dose distribution.

FIG. 1 illustrates ten 3-D CT data sets, acquired at ten phases throughout the breathing cycle. Each such data set can be used to generate phase-specific treatment plan. A 4-D CT (the fourth dimension being time) data set is obtained from multiple 3-D CT datasets acquired at different phases of the breathing cycle, and contains information of the anatomical changes of the target (e.g., tumor) and its surroundings over time. The actual breathing pattern of the patient at the time of treatment differs in general from the expected breathing patent obtained at the time of imaging. Accounting for the uniqueness of the breathing pattern at the time of treatment, while utilizing plans generated for a particular instance of breathing pattern, is the central premise of the current disclosure. The differences between the expected breathing pattern at the time of imaging and the actual breathing pattern at the time of treatment include two aspects: the duration of each breathing cycle and the amplitude of each breathing cycle.

Figure 2:
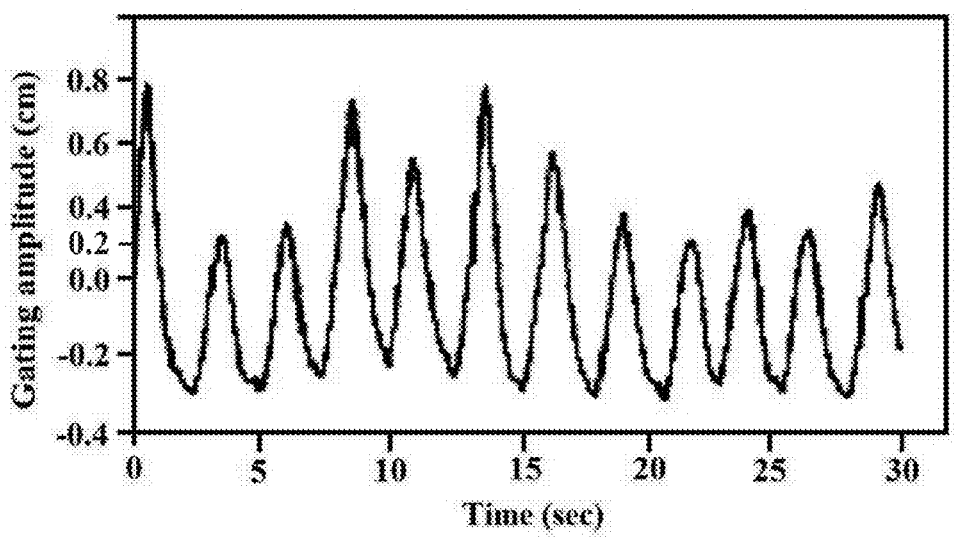
FIG. 2 is a graph of gating amplitude (cm) versus time (sec).

Rather than using a pre-programmed MLC movement sequence, BSTT controls the treatment machine and the MLC directly using a breathing signal, such as the one shown in FIG. 2). Rather than devising a fixed sequence of beam shape, location and orientation as a function of the accumulated MUs delivered, BSTT delivers radiation having parameters (e.g., beam shapes, locations, and orientations) as a function of breathing amplitude and phase at any point in a specific breathing cycle. Beam parameters as a function of phase/amplitude can be contained in a look-up table utilized by the treatment delivery control system.

In order not to miss any out-of-scope amplitude due to occasional deep breathing, the patient is asked to take a deep inhale and a deep exhale during imaging so that extreme positions can be established for the look-up table. Alternatively to imaging a deep inhalation and a deep exhalation, a relationship between the breathing pattern and the target shape and location can be extrapolated using geometric modeling, such as finite element analysis and optical flow algorithms. Since a patient is not likely to spend a significant amount of time inhaling or exhaling deeply during treatment, the dosimetric consequence of small tracking errors at such extreme positions is acceptably small. Because there are typically only about 8-10 image sets in a 4-D CT scan, each corresponding to a time sample in a breathing period, the number of elements in the look-up table is typically only about 10-12, with the additional two samples corresponding to the extreme positions of deep inhalation and deep exhalation. A small look-up table can be easily handled by today's computers used for linac/MLC controls, and the time required for loading the next point is so small as to be essentially negligible (less than several milliseconds) in comparison with the sampling interval of a few hundred milliseconds. During radiotherapy treatment, the detected breathing signals may contain points beyond the two extreme magnitudes, such as during a cough or yarning, although with even shorter time periods relative to the entire treatment delivery. In such cases, the nearest extreme point in the look-up table should be used as a substitute.

Still further provided is a system for controlling delivery of radiation by a radiation delivery device to a moving target in a patient in accordance with a radiation treatment plan. The system comprises: (i) a processor, which receives and processes data on the actual breathing of the patient or the shape and/or location of the target, wherein the data on the actual breathing of the patient includes breathing frequency and breathing amplitude, and (ii) a controller, which controls delivery of radiation by the radiation delivery device to the moving target in the patient in accordance with a radiation treatment plan, which defines the optimal shape and location of the radiation beam for each phase/amplitude of the actual breathing within a breathing cycle of the patient or the actual shape and/or location of the target during that phase of the breathing.

Preferably, and even desirably, the controller adjusts at least one optimal parameter for the delivery of radiation by the radiation delivery device to the moving target for each phase of the breathing cycle of the patient, wherein the optimal parameter is not enslaved to monitor units (MU). Preferably, and even desirably, the radiation treatment plan was prepared by a method comprising: (i) obtaining simultaneous data on the breathing of the patient and the tracking of a target in the patient, wherein the data on the breathing of the patient includes frequency of breaths and amplitude of breaths and the data on the tracking of a target includes location of the target and shape of the target, (ii) correlating the data on the breathing of the patient and the tracking of a target in the patient and optimizing the correlation, and (iii) establishing optimal parameters for the radiation to be delivered to the target in the patient in view of the optimized correlation of (ii).

The data of (i) can be previously generated using free-breathing imaging. The free-breathing imaging can be conducted using a four-dimensional (4-D) computed tomography (CT) scan.

The optimal parameters for the delivery of radiation to the target can be established based on a reference image set generated for an initial breathing phase using free-breathing imaging. The optimal parameters for the delivery of radiation to the target for a sequential breathing phase can be established using the optimal parameters for the initial breathing phase as initial input into an inverse planning algorithm, and the optimal parameters for each subsequent sequential breathing phase can be established using the optimal parameters for the previous sequential breathing phase, while enforcing a field connectivity constraint between the optimal parameters for immediately sequential breathing phases. The field connectivity constraint can be the shape of the field of radiation.

Alternatively, the optimal parameters for the delivery of radiation to the target can be established based on a reference image set generated for each phase of a breathing cycle using free-breathing imaging. A radiation dose efficiency index can be assigned to each phase of a breathing cycle, or the optimal parameters for the delivery of radiation to the target for each sequential breathing phase are established while enforcing a field connectivity constraint between immediately sequential breathing phases by applying an algorithm of directly transforming a parameter between immediately sequential breathing phases.

Figure 3:
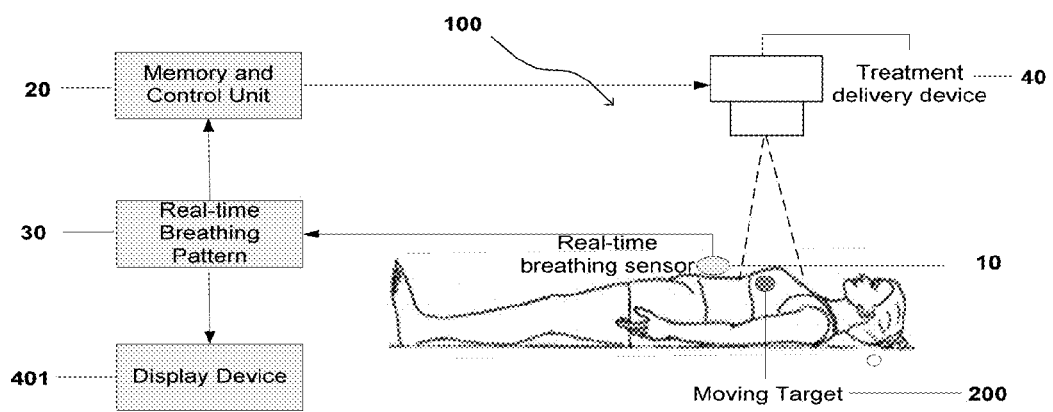
FIG. 3 illustrates an exemplary BSTT system (100) for delivering a radiation dose to a moving target (200) in a patient.
Figure 4:
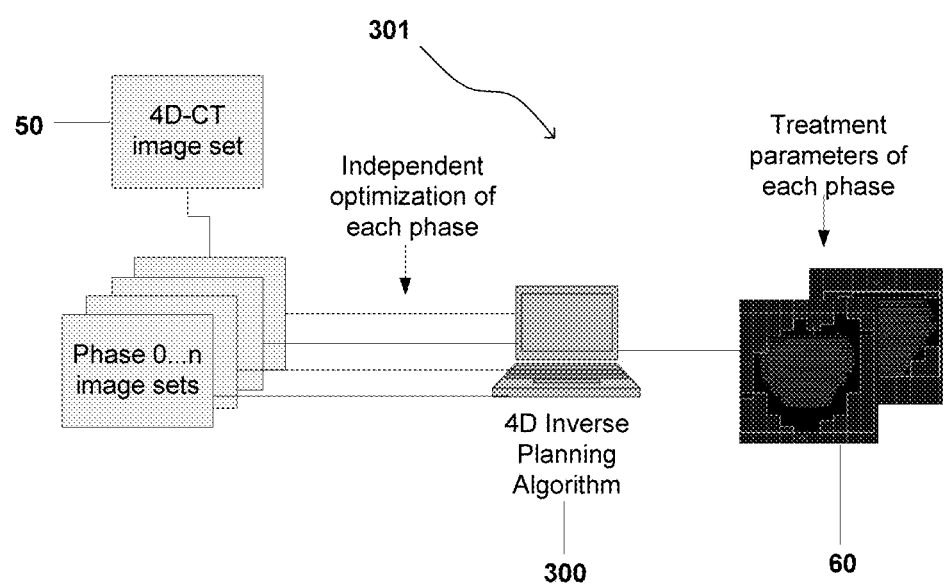
FIG. 4 is an exemplary conceptual diagram of the BSTT treatment planning process (301).

FIG. 3 illustrates an exemplary BSTT system (100) for delivering a radiation dose to a moving target (200), such as a tumor or organ, in a patient. The system includes a radiation delivery device (40), a real-time breathing monitor sensor (10), which is configured to obtain the real-time breathing pattern (30) for a patient in need of radiation therapy, a display device (401), and a memory and control unit (20). The measured breathing pattern (30) of the patient, which can be an averaged breathing pattern, is stored and processed in the memory and control unit (20). A display device (401) displays the real-time breathing pattern of the patient during the delivery of radiation. The radiation delivery device (40) is configured to deliver radiation in accordance with the 4-D inverse planning algorithm (300; FIG. 4) after the radiation delivery device (40) has been activated.

For BSTT, the 4-D treatment planning can be performed using the strategy shown in FIG. 4, which is an exemplary conceptual diagram of the BSTT treatment planning process (301). A 4D-CT image set (50), which comprises 3-D CT scans of breathing phases O-n, is fed into the 4-D BSTT treatment planning system (301). Typically a 4D-CT image set comprises "n" scans ranging from 1 to about 10, such as about 5 to about 10, e.g., about 8 to about 10, scans. The image set (60) for each breathing phase is independently optimized, a 4-D inverse planning algorithm (300) is applied, and a set of treatment parameters (such as field shape for each phase) is established for each phase (60). The inverse planning algorithm (300) ensures that the fields of the phases (60) are connected, e.g., the MLC shapes the fields of adjacent phases (60) so that they do not differ significantly and the field shape can be changed from one phase to the next in less time than the duration of the phase.

The proposed 4-D treatment planning method ensures that the plan quality is optimal for each individual phase, which can be done easily by optimizing each static plan independently on the 3-D CT image set of each breathing phase. Although in theory, simultaneously including the entire 4-D image sets in the optimization process has the potential benefit of mutual compensation among different phases, the overall composite plan quality using the proposed method is indistinguishable from the true global optimal if the individual plan for each phase is optimal. By removing the impacts of dose contributions from individual phases on the composite plan quality, delivery can be more flexible and planning can be less complex.

The BSTT planning method enables targeted tracking to be incorporated into intensity-modulated delivery. BSTT allows for each of the multiple segments within each beam used in intensity modulated radiation therapy (IMRT) to be treated in the same way as a single-aperture beam. Specifically, for each segment within a beam in a reference plan, phase-specific segments are cycled through during delivery. The intensity modulation can be achieved by planning on the reference phase similar to planning a conventional IMRT for a non-moving target. Beam shape, position, and orientation and the delivered MUs are planned according to the set of static images. Additionally, IMRT plans are generated for each phase using sets of static images for each phase. The dynamic tracking of the moving target is achieved through the transformation of the aperture in near real-time according to the phase and amplitude of breathing.

Unlike other tracking strategies, such as DRRT, in which the number of MUs delivered for each given breathing phase for a given aperture shape is pre-determined, only the total integrated dose for a given beam aperture is pre-determined in BSTT, and this dose can be delivered for any unique breathing pattern existing during a treatment delivery episode. For example, if the patient takes a longer pause at the end of one exhale, the radiation beam will stay at the corresponding location with a fixed aperture for a longer time. As a result, more MUs are delivered with this aperture at the end of exhale. Because the dose delivery does not assume a set number of MUs delivered in each phase the delivery accuracy of BSTT is independent of dose rates. There is no need for dose rate regulation, and the delivery is also immune to dose rate fluctuations. As long as the accumulated dose is kept track of during delivery of a beam/segment across multiple phases, dose rate may vary during delivery.

Because different beam/segment shapes will deliver a different integrated dose to the target per MU, track of integrated dose must be kept during delivery. For example, a small segment will deliver a smaller integrated dose per MU than a larger segment. Similarly, if the target moves to a greater depth during the breathing cycle a smaller integrated dose per MU will be delivered due increased beam attenuation. These factors are known a priori and the accumulated integrated dose can be tracked using a look-up table, via the duration of each phase interval during delivery. During delivery, the actual dose to the target, rather than the MU, is accumulated, and the treatment terminates according to the actual dose delivered to the target, rather than the total MU delivered.

Figure 5:
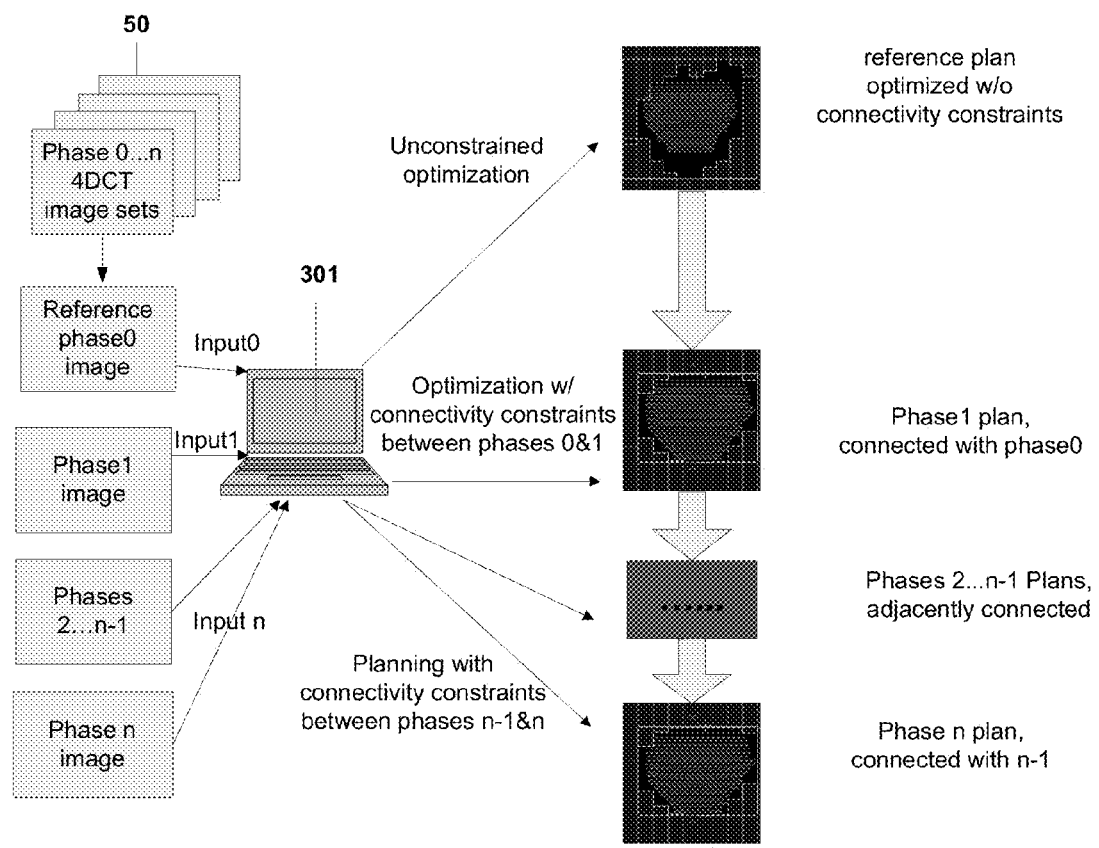
FIG. 5 is an exemplary conceptual diagram of the 4-D inverse planning method for BSTT.

FIG. 5 is an exemplary conceptual diagram of the 4-D inverse planning method for BSTT. Firstly, a static treatment plan is optimized for a reference phase/amplitude, which uses a static image set within the multiple (8-10) 4-D image sets corresponding to the different phases of the breathing cycle. This is referred to as "a reference plan". The reference plan is optimized, based on the reference phase image set without any constraints on the beam shapes. After the reference plan is created, a treatment plan for the next breathing phase/amplitude is independently optimized, while using the field shapes/locations/orientations information of the reference plan as initial input of the inverse planning, and at the same time enforcing the field connectivity constraints between plans of adjacent phases. Treatment plans for the remaining phases/amplitudes can be done in a similar fashion. Although the optimization with MLC connectivity constraints is a much more complex optimization problem than the unconstrained one, the complexity of the problem can be much reduced to a practically feasible level in accordance with the method set forth herein. Specifically, once the first phase is planned using a traditional, unconstrained optimization method, its result can be used as the initial guess in optimizing the next breathing phase. All remaining breathing phases can be optimized in a similar fashion. The treatment parameters, such as MLC shapes for adjacent breathing phases, are not expected to be significantly different because they are planned based on similar image sets. Therefore, an iterative optimization process, which starts from a benign initial guess close to the solution, can guarantee to converge to the solution quickly.

In an alternative embodiment, each phase can be assigned a different weight representing different "target-killing" or "normal-tissue-sparing" efficiency of the plan for that individual phase. Therefore, it is possible to deliver the radiation beam with a higher dose rate (MUs/min) at the more preferable phase if dose rate can be adjusted. As the result, more MUs are delivered in the phases that can produce better individual plan quality in terms of target coverage or critical organ sparing; and similarly fewer MUs are delivered in the phases with inferior dose efficiency. By dynamically changing the dose rates according to the dose-efficiency (or plan-quality) index of each individual phase, the composite plan can be further improved over the original plan. Also, by introducing more than one independent variable into the treatment delivery control, greater flexibility can be achieved without significantly increasing the complexity of the control system.

Figure 6:
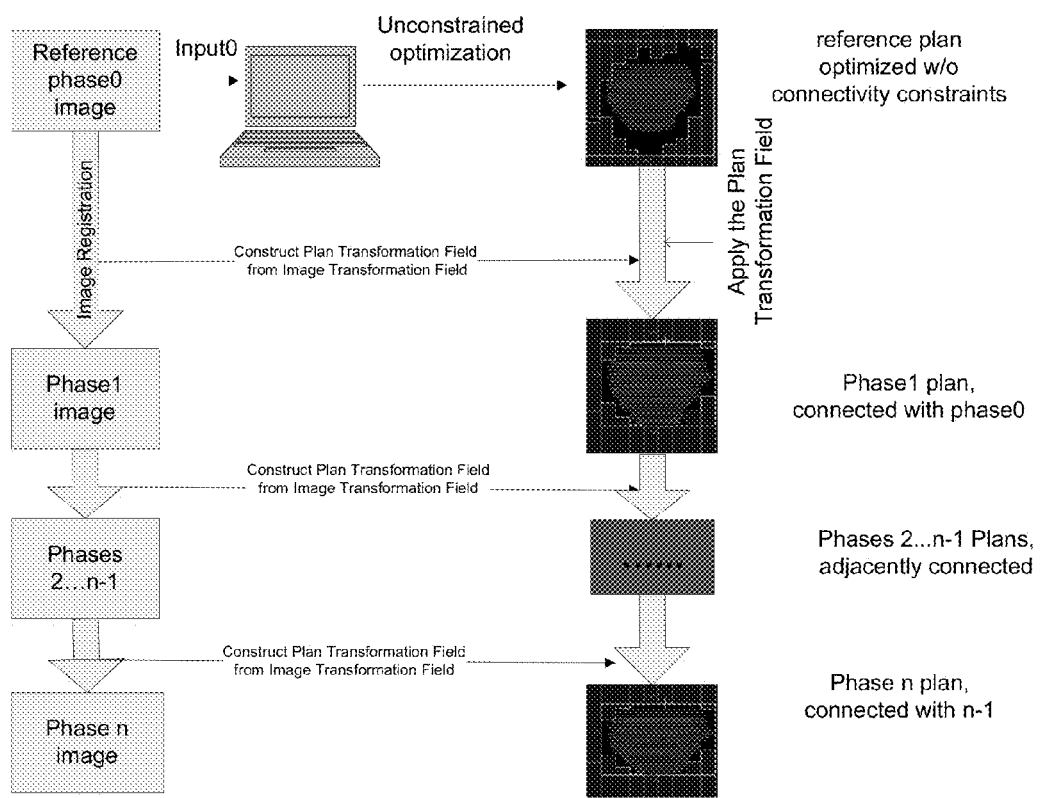
FIG. 6 is an exemplary conceptual diagram of an alternative planning method for BSTT.

Alternatively, the BSTT 4D planning can take the form of explicit operation on the treatment parameters directly as explained in FIG. 6, which is an exemplary conceptual diagram of an alternative planning method for BSTT. Firstly, a reference plan is optimized, based on the reference phase image set without any constraints on the beam shapes. Subsequently, the plans for the remaining breathing phases are optimized, while achieving connectivity between adjacent phases by an explicit algorithm of transforming the aperture directly. The transformation field between the treatment parameters of two adjacent phases ("plan transformation field") can be constructed from the transformation information between the 4-D images of the two corresponding images ("image transformation field") obtained via deformable image registration between the 4-D images of two adjacent phases. The transformation fields can include both rigid-body and non-rigid-body deformation components. Since the plan transformation field is explicitly applied to the previous phase plan to generate current phase plan, the inter-phase-connectivity can be easily and explicitly enforced. The algorithm to construct the plan transformation field based on image transformation field can be a set of ad hoc rules. The ad hoc rules of transforming/morphing the field parameters should ensure the shape changes between adjacent plans are "similar" to the shape changes between the corresponding adjacent images. The rules can be flexible and adaptive to different planning objectives.

In a preferred embodiment, the shape, location and orientation of the beam for each phase/amplitude are pre-optimized and stored in one look-up table. If the look-up table contains the treatment parameters of each phase, it can be loaded to the linac controller at the beginning of the treatment for the later employment of the parameters at each phase. During delivery, the to-be-delivered beam shape and location are pulled directly from the look-up table. In an alternative embodiment, the full field information of the reference phase is saved and resides in a look-up table loaded into the radiation delivery memory and control unit ((20); FIG. 3). The transformation vectors (shifts, deformations, and rotations) from this reference phase to other breathing phases or between adjacent phases are stored in a look-up table. The to-be-delivered beam shape and location information is obtained by transforming the reference or previous phase beam shape using the corresponding transformation vectors "on-the-fly". The transformation operation can be accomplished by a modern computer within a timeframe negligible in comparison to the time sample interval between the phases.

Whereas the delivery time of one aperture normally spans more than one respiratory phase in conventionally planned, intensity-modulated, radiation therapy (IMRT), multiple apertures corresponding to different phases should be sequentially delivered in order to account for target motion in one segment. This requires the optimized plan for each phase to have an identical number of apertures at the same beam angle. However, individually optimizing the treatment parameters on the 3-D CT dataset of each respiratory phase does not guarantee the same number of apertures for all phases, which makes the delivery inefficient, if not impossible. Furthermore, there are no geometrical relationships for the apertures between adjacent phases. As such, individually optimized beam apertures using a conventional inverse planning algorithm on each 3-D CT image set corresponding to each breathing phase are not guaranteed to be connected due to the mechanical speed limit of the MLC leaves, which is a main obstacle in conventional 4-D IMRT planning.

The BSTT planning algorithm solves these problems by considering the MLC connectivity while optimizing the treatment parameters including the field shapes/locations for the best plan quality (dose distribution) for each individual phase data set. Therefore, in a BSTT plan, the MLC aperture shapes for any two adjacent phases are always connected, meaning the time it takes to transform the aperture shape from current phase to the next phase is always less than the duration of the breathing phase. This feature of the optimization can be easily implemented based on conventional optimization algorithms. Field parameters between adjacent phases do not differ significantly so that the MLC connectivity is preserved after optimization of individual phases. In addition, the number of segments for each individual phase plan can be controlled to be equal, which makes it possible for the 4-D treatment delivery of a preplanned step-and-shoot IMRT plan.

The treatment planning generates a set of control points (field shapes) for each of the breathing phases between the two extreme phases. The planning algorithm ensures that, at a given planned beam angle, the field shapes of any adjacent two breathing phases are always connected. Although the treatment parameters stored in the look-up table have no explicit connection to each other, it is impossible for the control points not to be connected because the breathing signal is always a continuous function, i.e., one cannot breathe by jumping a phase.

The final aspect of the BSTT 4-D treatment plan includes multiple control points for each planned beam angle and segment, where each control point directly correlates with the breathing amplitude/phase determined by the real-time breathing monitoring device during treatment. Unlike a traditional RT plan, each control point in a BSTT plan is not associated with a pre-determined amount of radiation (MU). Instead, during a BSTT delivery, a flexible and un-planned amount of MU is delivered for each control point.

The delivered MU of each control point is dependent on the actual dwelling time of the corresponding breathing phase, which is determined "on-the-fly" by the breathing monitoring device. Each control point of BSTT does not require the enslavement to MU as does traditional radiation therapy plan delivery. Because each individual phase is independently optimized, by doing so the final composite plan quality will not be significantly altered whether more or less MUs are delivered to certain breathing phases relative to other phases, as long as the total integrated dose across all breathing phases is delivered as planned. What is important for plan quality is that the beam/segment shape during any interval of time is consistent with that for the optimized plan for the phase interval corresponding to that time interval.

The decoupling of accumulated MU and beam parameters offers another opportunity to improve further the composite 4-D dose distribution by delivering more dose during the phases when the anatomy is more favorable. For example, this may be when the target and critical organs are more separated or a critical organ moves out of the beam path during breathing. It may also be when the target is at a phase corresponding to minimal motion, such as near full exhale. Although each phase is individually optimized, the plan quality in terms of target coverage or critical organ sparing can differ significantly between phases. In this alternative embodiment of BSTT, dose rates for the control points corresponding to different breathing phases are assigned with different weightings, allowing the target to receive more dose at favorable phases. The plan-quality can be quantified using a weighting factor or plan-quality index. It is, therefore, straightforward to improve upon the constant dose-rate BSTT by delivering relatively more dose to the phase with a higher plan-quality index. This can be implemented on BSTT by adjusting the dose rate (MU/min) for each breathing phase, which is proportional to the weight of that particular phase.

In contrast to traditional radiation therapy delivery, there is no pre-determined amount of radiation (MU) associated to each control point of BSTT. All other treatment parameters of BSTT, such as field shape, are directly driven by the patient breathing signal detected in real-time. Table 1 shows parameters stored in the machine controller memory for a traditional radiation therapy plan, such as the leaf position of the MLC, field size (or collimator opening), gantry angle, table position, and collimator angle, etc., are enslaved to MU. Table 1 also shows parameters stored in the memory and control unit ((20); FIG. 3) for a BSTT treatment plan, which are not enslaved to MU; rather the parameters are enslaved to the patient breathing signal detected in real-time. A flexible amount of MU can be delivered for each control point, depending on the actual dwelling time of the corresponding breathing phase detected "on-the-fly".

TABLE 1

| Conventional Treatment Parameters | BSTT Treatment Parameters |
|---|---|
| MU to be delivered for this control point | Breathing signal for this control point |
| Field size | Field size |
| Collimator angle | Collimator angle |
| MLC positions | MLC positions |
| Couch angle | Couch angle |
| . . . | . . . |
| Total MU for the segment | Total MU for the segment |

Figure 7:
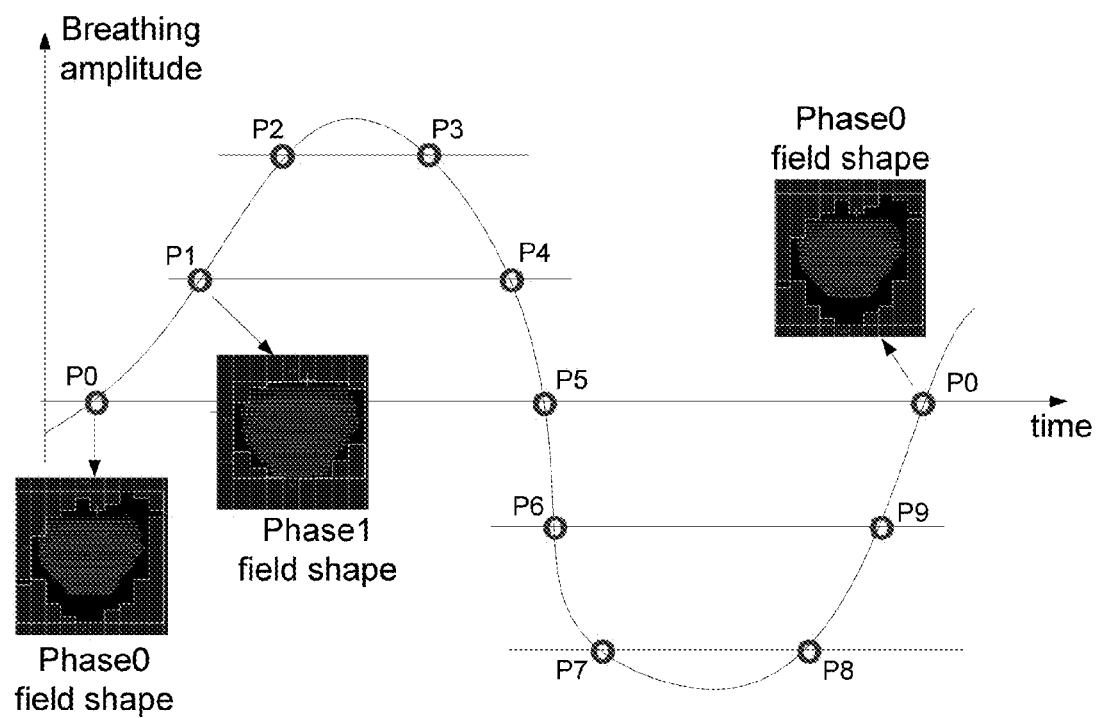
FIG. 7 is an exemplary conceptual diagram of BSTT delivery based on real-time patient breathing.

FIG. 7, which is an exemplary conceptual diagram of BSTT delivery based on real-time patient breathing, illustrates how the beam apertures formed by an MLC are configured at different phases during radiation treatment delivery "on-the-fly". The MU of each aperture is determined on-the-fly, depending on the actual time span of that breathing phase during treatment. Since the actual time spans between certain phases (e.g., P0, P1, P2, and P3) are much longer than those between other phases (e.g., P4, P5, P6, and P7), the actual doses and MUs delivered in phases 0 through 3 are higher than those delivered in phases 4 through 7. Because the treatment plan for each individual phase is independently optimized, the flexibility in the amount of MUs delivered to any single breathing phase will not significantly alter the composite plan quality as long as the total integrated dose for a given segment is delivered as planned.

In an exemplar BSTT treatment delivery, the patient takes a longer pause at the end of exhale. In such case, the radiation beam will stay at the corresponding exhale location with corresponding aperture for a longer time than at other locations. As the result, more MUs will be delivered with this aperture at the end of exhale than other phases. In contrast to DRRT, BSTT can be delivered using constant dose rate. Because the dose delivery is not linked to the MUs delivered in each phase, the delivery accuracy of BSTT is also independent of dose rates. Therefore, there is no need for dose rate regulation, and the delivery is immune to dose rate fluctuations.

All patents, patent application publications, journal articles, textbooks, and other publications mentioned in the specification are indicative of the level of skill of those in the art to which the invention pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" include one or more methods and/or steps of the type described herein and/or apparent to those ordinarily skilled in the art upon reading the disclosure.

The terms and expressions, which have been employed, are used as terms of description and not of limitation. In this regard, where certain terms are defined and otherwise described or discussed elsewhere herein, all such definitions, descriptions, and discussions are intended to be attributed to such terms. There also is no intention in the use of such terms and expressions of excluding any equivalents of the features shown and described or portions thereof.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

What is claimed is:

1. A method of preparing a plan to synchronize delivery of radiation to a target in a patient, wherein the method comprises:
   (a) obtaining simultaneous imaging data on the patient's breathing and tracking of the target in the patient, wherein the data on the breathing of the patient includes the phase and amplitude of breaths and the data on the tracking of the target includes a location of the target and a shape of the target,
   (b) correlating the data on the breathing of the patient and the data on the tracking of the target in the patient and optimizing the correlation,
   whereupon a three-dimensional image of the patient for each phase/amplitude of breath is generated, and
   (c) establishing optimal parameters for the delivery of radiation by a machine to the target in the patient for each phase/amplitude of breath in view of the optimized correlation of (b),
   whereupon a look-up table for the plan of synchronizing delivery of radiation to the target in the patient is prepared.

2. The method of claim 1, wherein the data were previously generated using free-breathing imaging and deep-breathing imaging.

3. The method of claim 2, wherein the free-breathing imaging and deep-breathing imaging was conducted using a four-dimensional (4-D) computed tomography (CT) scan.

4. The method of claim 2, wherein the optimal parameters for the delivery of radiation by the machine to the target are established based on a 4-dimensional reference image set.

5. The method of claim 4, wherein the optimal parameters for the delivery of radiation by the machine to the target for a sequential breathing phase are established using optimal parameters for an initial breathing phase as initial input into an inverse planning algorithm and optimal parameters for each subsequent sequential breathing phase are established using optimal parameters for a previous sequential breathing phase while enforcing a field connectivity constraint between optimal parameters for immediately sequential breathing phases.

6. The method of claim 5, wherein the field connectivity constraint is the shape of the field of radiation.

7. The method of claim 4, wherein the optimal parameters for the delivery of radiation to the target are established by assigning a radiation dose efficiency index to each phase of a breathing cycle.

8. The method of claim 4, wherein the optimal parameters for the delivery of radiation to the target for each sequential breathing phase are established while enforcing a field connectivity constraint between immediately sequential breathing phases by applying an algorithm of directly transforming a parameter between the immediately sequential breathing phases.

9. A method of synchronizing delivery of radiation to a target in a patient with breathing of the patient, wherein the method comprises:
   (a) positioning the patient for delivery of radiation to the target in the patient,
   (b) either monitoring the breathing of the patient in real time via an external indicator of internal target motion or monitoring directly in real time the shape and/or location of the target within the patient, and
   (c) while continuing to monitor the breathing of the patient or the shape and location of the target in the patient, loading optimal parameters onto a machine for delivery of radiation to the target in the patient according to a look-up table for a radiation treatment plan in view of the breathing of the patient or the shape and location of the target, wherein the look-up table for the radiation treatment plan was prepared by a method comprising:
      (i) obtaining simultaneous imaging data on the breathing of the patient and tracking of the target in the patient,
         wherein the data on the breathing of the patient includes the phase and amplitude of breaths and the data on tracking of the target includes location of the target and shape of the target,
      (ii) correlating the data on the breathing of the patient and the data on the tracking of the target in the patient and optimizing the correlation,
         whereupon a three-dimensional image of the patient for each phase/amplitude of breath is generated, and
      (iii) establishing optimal parameters for the delivery of radiation by the machine to the target in the patient for each phase/amplitude of breath in view of the optimized correlation of (ii),
      whereupon delivery of radiation to the target in the patient is synchronized with breathing of the patient.

10. The method of claim 9, wherein the data of (i) were previously generated using free-breathing imaging and deep-breathing imaging.

11. The method of claim 10, wherein the free-breathing imaging and deep-breathing imaging was conducted using a 4-D CT scan.

12. The method of claim 10, wherein the optimal parameters for the delivery of radiation by the machine to the target were established based on a 4-dimensional reference image set.

13. The method of claim 12, wherein the optimal parameters for the delivery of radiation by the machine to the target for a sequential breathing phase were established using optimal parameters for an initial breathing phase as initial input into an inverse planning algorithm and optimal parameters for each subsequent sequential breathing phase were established using optimal parameters for a previous sequential breathing phase while enforcing a field connectivity constraint between optimal parameters for immediately sequential breathing phases.

14. The method of claim 13, wherein the field connectivity constraint is the shape of the field of radiation.

15. The method of claim 12, wherein the optimal parameters for the delivery of radiation to the target were established by assigning a radiation dose efficiency index to each phase of a breathing cycle.

16. The method of claim 12, wherein the optimal parameters for the delivery of radiation to the target for each sequential breathing phase are established while enforcing a field connectivity constraint between immediately sequential breathing phases by applying an algorithm of directly transforming a parameter between the immediately sequential breathing phases.

\* \* \* \* \*

UNITED STATES PATENT AND TRADEMARK OFFICE
CERTIFICATE OF CORRECTION

PATENT NO. : 9,504,850 B2
APPLICATION NO. : 14/201906
DATED : November 29, 2016
INVENTOR(S) : Jin Zhang et al.

It is certified that error appears in the above-identified patent and that said Letters Patent is hereby corrected as shown below:

In the Claims

In Column 17, Line 19, the first line of Claim 1 should read as follows:

--1. A method of preparing a look-up table for a plan to synchronize delivery--

Signed and Sealed this
Twenty-eighth Day of March, 2017

Michelle K. Lee
*Director of the United States Patent and Trademark Office*